(12) United States Patent
Tsai et al.

(10) Patent No.: US 7,342,146 B2
(45) Date of Patent: Mar. 11, 2008

(54) NEURODEGENERATIVE NON-HUMAN TRANSGENIC MAMMAL EXPRESSING TRKA FUSION PROTEIN

(75) Inventors: Yuan-Jang Tsai, Sinpu Township, Hsinchu County (TW); Chrong-Shiong Hwang, Hsinchu (TW); Shing-Mein Wu, Dashe Township, Kaohsiung County (TW); Yen-Chun Chen, Hsinchu (TW); Chen-Yi Su, Hsinchu (TW); Tsan-Lin Hu, Pingtung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/330,821

(22) Filed: Jan. 11, 2006

(65) Prior Publication Data

US 2007/0162990 A1    Jul. 12, 2007

(51) Int. Cl.
*G01N 33/00* (2006.01)
*A01K 67/00* (2006.01)
*A01K 67/027* (2006.01)
*C07H 21/02* (2006.01)
*C07H 21/04* (2006.01)

(52) U.S. Cl. ................. 800/18; 800/3; 800/9; 536/23.1
(58) Field of Classification Search .................... 800/3, 800/9, 18; 536/23.1
See application file for complete search history.

(56) References Cited

OTHER PUBLICATIONS

Schonheit et al., 2004, Neurobiology of Aging, 25: 697-711.*
Franz et al., 1997, J. Mol. Med., 75: 115-129.*
Racay, 2002, Bratisl Lek Listy, 103: 121-126.*
Rita Levi-Montalcini et al., "Effects of Mouse Tumor Transplantation on the Nervous System" Western Journals, Annals of the New York Academy of Sciences, vol. 55, Art 3, 1952, pp. 330-334.
Satoshi Morimoto et al., "Elevated Blood Pressure in Transgenic Mice With Brain-Specific Expression of Human Angiotensinogen Driven by the Glial Fibrillary Acidic Protein Promoter" Circulation Research Journal of the American Heart Association, Aug. 17, 2001, pp. 365-372.
Giorgio Palu et al., "Gene Therapy of Brain and Endocrine Tumors" Croatian Medical Journal, vol. 42, No. 4, 2001, pp. 473-477.
Jose Segovia et al., "Differentiation-dependent expression of transgenes in engineered astrocyte cell lines" Neuroscience Letter, vol. 242, 1998, pp. 172-176.
Ningya Shi et al., "Brain-specific expression of an exogenous gene after l.v. administration" PNAS, vol. 98, No. 22, Oct. 23, 2001, pp. 12754-12759.
Absalom Zamorano et al., "Transcriptionally Mediated Gene Targeting of gas1 to Glioma Cells Elicits Growth Arrest and Apoptosis" Journal of neuroscience Research, vol. 72, 2003, pp. 256-263.
Eric J. Huang et al., "Neurotrophins: Roles in Neuronal Development and Function" Annual Review of Neuroscience; 2001, vol. 24 ProQuest science Journals, pp. 677-736.
Ardem Patapoutian et al., "Trk receptors: mediators of neurotrophin action" Current Opinion in Neurobiology 2001, vol. 11, pp. 272-280.
Elliott J. Mufson et al., "Reduction in P140-TrkA Receptor Protein within the Nucleus Basalis and Cortex in Alzheimer Disease" Experimental Neurology 146, 1997, pp. 91-103.
Esperanza Arias, et al., "Unequal Neuroprotection Afforded by the Acetylcholinesterase Inhibitors Galantamine, Donepezil, and Rivastigmine in SH-SY5Y Neuroblastoma Cells: Role of Nicotinic Receptors" The Journal of Pharmaology and Experimental Therapeutics 2005, vol. 315, No. 3, pp. 1346-1353.
Christopher Janus et al., "Transgenic mouse models of Alzheimer's disease" Physiology & Behavior 2001, vol. 73, pp. 873-886.
Jonathan D. Cooper et al., "Failed retrograde transport of NGF in a mouse model of Down's Syndrome: Reversal of cholinergic neurodegenerative phenotypes following NGF Infusion" PNAS, Aug. 28, 2001, vol. 98, No. 18, pp. 10439-10444.
Brian J. Hock et al., "Transgenic mouse models of Alzheimer's Disease" TRENDS in Genetics, vol. 17, No. 10, Oct. 2001, pp. S7-S12.

* cited by examiner

*Primary Examiner*—Anne M. Wehbe
*Assistant Examiner*—Joanne Hama
(74) *Attorney, Agent, or Firm*—J.C. Patents

(57) ABSTRACT

The present invention provides a neurodegenerative, non-human transgenic mammal whose cells contain a TrkA-hFc transgene for encoding at least a TrkA fusion protein and the use thereof.

4 Claims, 5 Drawing Sheets

SEQUENCE LISTING

```
<160> NUMBER OF SEQ ID NOS: 1

<210> SEQ ID NO 1
<211> LENGTH: 1434
<212> TYPE: DNA
<213> ORGANISM: Artificial
<220> FEATURE:
<223> OTHER INFORMATION: mTrkA-hFc construct

<400> SEQUENCE: 1
atgtctgcac ttctgatcct agctcttgtt ggagctgcag ttgctgacta caaagacgat      60
gccctgttct ggctccagcg ttgggagcag gaaggactgt gtggtgtgca tacacagacg     120
cttcatgact ctgggcctgg agaccagttc ctcccactgg gacacaacac tagttgtggt     180
gtacccacag tgaagatcca gatgcccaat gactctgtgg aagtgggcga tgacgtgttt     240
ctgcagtgcc aggtggaggg gctggcccta cagcaggctg actggatcct cacagagctg     300
gaaggggcag ccaccgtgaa gaaatttgga gatctgccat ccctggggct gattctggtc     360
aatgtcacca gtgatctcaa caagaagaat gcgacgtgct gggcagagaa tgatgtgggc     420
cgggccgagg tctctgtcca agtcagcgtc tccttcccag ccagtgtgca cctgggccta     480
gcggtggagc agcatcattg gtgcatcccc ttctcggtgg acgggcagcc agcaccgtct     540
ctgcgctggt tgttcaacgg ctctgtgctc aacgagacca gtttcatctt cactcagttc     600
ttggagtctg cgctgactaa tgagaccatg cggcacggct gcctgcgcct caatcagccc     660
acgcatgtca caacgggaa ctacaccggg tacccgaatc acaagcccag caacaccaag     720
gtggacaaga gagttgagcc caaatcttgt gacaaaactc acacatgccc accgtgccca     780
gcacctgaac tcctgggggg accgtcagtc ttcctcttcc ccccaaaacc caaggacacc     840
ctcatgatct cccggacccc tgaggtcaca tgcgtggtgg tggacgtgag ccacgaagac     900
cctgaggtca agttcaactg gtacgtggac ggcgtggagg tgcataatgc caagacaaag     960
ccgcgggagg agcagtacaa cagcacgtac cgtgtggtca gcgtcctcac cgtcctgcac    1020
caggactggc tgaatggcaa ggagtacaag tgcaaggtct ccaacaaagc cctcccagcc    1080
cccatcgaga aaaccatctc caaagccaaa ggcagcccc gagaaccaca ggtgtacacc    1140
ctgcccccat cccgggatga gctgaccaag aaccaggtca gcctgacctg cctggtcaaa    1200
ggcttctatc ccagcgacat cgccgtggag tgggagagca atgggcagcc ggagaacaac    1260
```

```
tacaagacca cgcctcccgt gctggactcc gacggctcct tcttcctcta cagcaagctc    1320
accgtggaca agagcaggtg gcagcagggg aacgtcttct catgctccgt gatgcatgag    1380
gctctgcacc accactacac gcagaagagc ctctccctgt ctccgggtaa atga          1434
```

NEURODEGENERATIVE NON-HUMAN TRANSGENIC MAMMAL EXPRESSING TRKA FUSION PROTEIN

BACKGROUND OF THE INVENTION

1. Field of the Invention

The present invention generally relates to a neurodegenerative non-human transgenic animal. In particular, the present invention relates to a neurodegenerative non-human transgenic mammal expressing the TrkA recombinant protein and the use thereof.

2. Description of Related Art

As the median of the industrialized world's population increases gradually, age-related diseases are becoming a major public health challenge. Most significantly, neurodegenerative diseases affect a large sector of the elderly population. Alzheimer's disease (AD) is the most common neurodegenerative disorder and the most common cause of dementia. AD is typified by progressive memory loss, impairment in judgment, decision making, orientation and language. On the cellular level, AD is characterized by the deposition of amyloid plaques outside nerve cells, the accumulation of abnormal protein filaments inside nerve cells in the brain and neuronal loss. Epidemiology studies indicate that Alzheimer's diseases alone affect about one tenth of the population over 65 years of age. For example, in the United States, more than four millions people suffer from the disease, and the economic impact of the disease exceeds billions of dollars. It is estimated that by the year of 2025, more than 22 millions of the world population will be inflicted with some forms of Alzheimer's disease. Therefore, the developments of effective prevention methods and cures are imminently required.

Currently, means for an early diagnosis and an appropriate treatment of the various neurodegenerative diseases such as AD are lacking. A development of a drug or animal model is essential for studying the mechanisms underlying AD and testing the efficacy of new drugs. The unavailability of a suitable animal model hampers the screening of new therapeutic agents. The current animal models are transgenic animals produced with mutated genes from familial Alzheimer's, which can only represent 5% of the AD patients. Absence of a comprehensive model for AD, the development of new drugs and defining the etiopathogenesis of the disease will be limited.

Nerve growth factor (NGF) (Levi-Montaicini, 1952, "Effects of mouse tumor transplantation on the nervous system" Ann N Y Acad Sci. 55(2):330-44) is a member of a family of peptides known as neurotrophins which are essential in the developments and survival of certain sympathetic and sensory neurons in both the central and peripheral nervous systems. Other members of the neurotrophin family include brain-derived neurotrophic factor (BDNF), neurotrophin 3 (NT-3), and neurotrophin 4 (NT-4). There are two classes of receptors, p75 and the Tyrosine kinases. The receptor p75 is a low affinity neurotrophin receptor, to which all neurotrophins bind. The Tyrosine kinases include TrkA, TrkB, and TrkC, and will only bind with specific neurotrophins at a higher affinity. NGF binds to two classes of cells surface receptors: the p75 receptor and the TrkA receptor. The binding of NGF to TrkA initiates the neuronal signaling pathway. BDNF and NT-4 bind to TrkB receptors while NT-3 specifically interacts with TrkC receptors. However, NT-3 can also activate TrkA and TrkB receptors under certain conditions. Similarly, NT-4 also binds to TrkA with lower affinity.

Trangenic animals lacking sufficient nerve growth factor (NGF) suffer from neruoronal damage and behavioral disorder. Depletion of extracellular NGF by the administration of neutralizing antibodies (anti-NGF) has been shown to result in a neurodegenerative phenotype resembling AD in aged transgenic animal model. However, such a model can only focus on the signaling pathway of NGF. On the other hand, a Trk receptor deficient animal model may provide a more comprehensive understanding on the tropic actions of the various neurotrophins.

SUMMARY OF THE INVENTION

The present invention provides a neurodegenerative, non-human transgenic mammal whose cells contain a recombinant DNA sequence (the TrkA-hFc transgene) for encoding at least a TrkA fusion protein or a defective TrkA receptor.

The transgenic mammal provided by this invention can be useful as models for disease and for identifying agents that modulate gene expression and gene function, and as potential treatments for various disease states and disease conditions.

As embodied and broadly described herein, the transgenic mammal provided by this invention is useful for studies on neurotrophins and also useful for identifying agents or compounds that modulate the biological functions of a Trk receptor, including the screening and identification of potential therapeutic agents or compounds.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
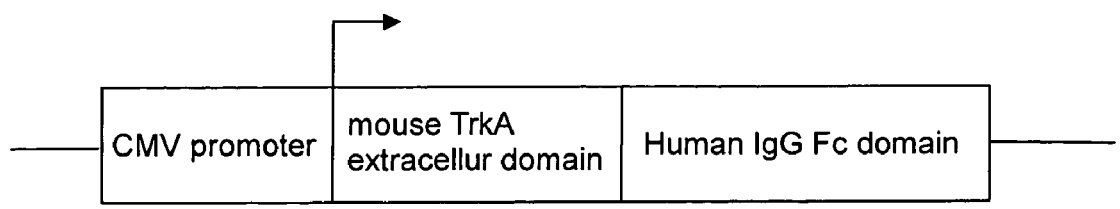
FIG. 1A is the gene map of the mTrkA transgenic vector with the CMV promoter.

Reference will now be made in detail to the present preferred embodiments of the invention, examples of which are illustrated in the accompanying drawings. Wherever possible, the same reference numbers are used in the drawings and the description to refer to the same or like parts.

The present invention provides a neurodegenerative, non-human transgenic mammal model whose cells contain at least a recombinant DNA sequence (a transgene).

The term "transgenic animal" refers to an animal that contains within its genome the specific transgene. The transgenic animal includes both the heterozygote animal (i.e., one defective allele and one wild-type allele) and the homozygous animal (i.e., two defective alleles).

The term "gene" refers to (a) a gene containing at least one of the DNA sequences disclosed herein; (b) any DNA sequence that encodes the amino acid sequence encoded by the DNA sequences disclosed herein and/or; (c) any DNA sequence that hybridizes to the complement of the coding sequences disclosed herein. Preferably, the term includes coding as well as noncoding regions.

The transgenic animal model may be established following at least the procedures of transgenic vector construction, transgenic mice production, and transgenic animal genotype verification (behavior and pathology). The details of these procedures will be described in more details hereinafter.

According to one embodiment of this invention, a Trk receptor deficient animal model is provided through microinjection with the transgene comprising the gene encoding the TrkA extracellular domain protein (TrkA extracellular domain gene) and the gene encoding the constant region (Fc) of the immunoglobulin (Fc gene), suitable for potential studies on various neurotrophins or diseases in related with neurotrophins.

I. TrkA-trap Transgene Construct:

(1) mTrkA Gene Construction:

Mouse brain cDNA is used as a template in the PCR (polymerase chain reaction) for amplifying the mouse TrkA (mTrkA) extracellular domain gene (DNA segment expressing the mTrkA extraxcelluar domain protein). The primers (forward, [SEQ ID NO. 2], 5' ACCCACTGCATTGTTC-CTGT 3'; reverse, [SEQ ID NO. 3], 5' GGTGTAGTTC-CCGTTGTTGAC 3') are designed base on the reference sequence of the mouse TrkA cDNA nucleotide sequence (GeneBank access number: XM283871). PCR is then performed to amplify the mTrkA DNA segment with the following parameters: 95° C. for 2 min, then 32 cycles with denaturation step at 95° C. for 30 sec, hybridization at 55° C. for 30 sec, and elongation at 72° C. for 1 min, with a final elongation at 72° C. for 5 min. The amplified PCR product (647 base pairs), the mTrkA extracellular domain gene, is then cloned into the pGEMt vector (purchased from Promega, Madison, Wis.) using TA cloning technology. Nucleotide sequence analysis is then performed to confirm the DNA sequence of the mTrkA/pGEMt vector.

(2) Human Fc (hFc) Gene Construction

Human lymphocyte cDNA is used as a template for amplifying the human Fc (hFc) gene (DNA segment expressing the Fc region of human immunoglobulin G). The primers (HFc-for, [SEQ ID NO. 4], 5' TGAATCACAAGC-CCAGCAACACCAA 3'; HFc-rev, [SEQ ID NO. 5], 5' GCCGGCCGTCGCACTCATTTAC 3') are designed base on the reference sequence of the human IgG nucleotide sequence (GeneBank access number: AF150959). PCR is then performed to amplify the human Fc DNA segment. The hFc gene and the mTrkA/pGEMt vector are ligated under the action of restriction enzyme and ligase. Nucleotide sequence analysis is then performed to confirm the DNA sequence of the mTrkA-hFc/pGEMt vector. The mTrkA-hFc gene is referred as TrkA-trap gene or TrkA-trap transgene hereinafter. The DNA sequences of the resultant construct mTrkA-hFc (SEQ ID NO. 1):

```
ATGTCTGCACTTCTGATCCTAGCTCTTGTTGGAGCTGCAGTTGCTGACT

ACAAAGACGATGCCCTGTTCTGGCTCCAGCGTTGGGAGCAGGAAGGAC

TGTGTGGTGTGCATACACAGACGCTTCATGACTCTGGGCCTGGAGACC
```

-continued
```
AGTTCCTCCCACTGGGACACAACACTAGTTGTGGTGTACCCACAGTGA

AGATCCAGATGCCCAATGACTCTGTGGAAGTGGGCGATGACGTGTTTC

TGCAGTGCCAGGTGGAGGGGCTGGCCCTACAGCAGGCTGACTGGATCC

TCACAGAGCTGGAAGGGGCAGCCACCGTGAAGAAATTTGGAGATCTG

CCATCCCTGGGGCTGATTCTGGTCAATGTCACCAGTGATCTCAACAAG

AAGAATGCGACGTGCTGGGCAGAGAATGATGTGGGCCGGGCCGAGGT

CTCTGTCCAAGTCAGCGTCTCCTTCCCAGCCAGTGTGCACCTGGGCCTA

GCGGTGGAGCAGCATCATTGGTGCATCCCCTTCTCGGTGGACGGGCAG

CCAGCACCGTCTCTGCGCTGGTTGTTCAACGGCTCTGTGCTCAACGAGA

CCAGTTTCATCTTCACTCAGTTCTTGGAGTCTGCGCTGACTAATGAGAC

CATGCGGCACGGCTGCCTGCGCCTCAATCAGCCCACGCATGTCAACAA

CGGGAACTACACCGGGTACCCGAATCACAAGCCCAGCAACACCAAGG

TGGACAAGAGAGTTGAGCCCAAATCTTGTGACAAAACTCACACATGCC

CACCGTGCCCAGCACCTGAACTCCTGGGGGACCGTCAGTCTTCCTCTT

CCCCCCAAAACCCAAGGACACCCTCATGATCTCCCGGACCCCTGAGGT

CACATGCGTGGTGGTGGACGTGAGCCACGAAGACCCTGAGGTCAAGTT

CAACTGGTACGTGGACGGCGTGGAGGTGCATAATGCCAAGACAAAGC

CGCGGGAGGAGCAGTACAACAGCACGTACCGTGTGGTCAGCGTCCTCA

CCGTCCTGCACCAGGACTGGCTGAATGGCAAGGAGTACAAGTGCAAG

GTCTCCAACAAAGCCCTCCCAGCCCCCATCGAGAAACCATCTCCAAA

GCCAAAGGGCAGCCCCGAGAACCACAGGTGTACACCCTGCCCCCATCC

CGGGATGAGCTGACCAAGAACCAGGTCAGCCTGACCTGCCTGGTCAAA

GGCTTCTATCCCAGCGACATCGCCGTGGAGTGGGAGAGCAATGGGCAG

CCGGAGAACAACTACAAGACCACGCCTCCCGTGCTGGACTCCGACGGC

TCCTTCTTCCTCTACAGCAAGCTCACCGTGGACAAGAGCAGGTGGCAG

CAGGGGAACGTCTTCTCATGCTCCGTGATGCATGAGGCTCTGCACCAC

CACTACACGCAGAAGAGCCTCTCCCTGTCTCCGGGTAAATGA
```

(3) mTrkA Transgenic Vector Construction:

The mTrkA-hFc/pGEMt vector is used as a template to design the PCR primer (Hind III-F [SEQ ID NO. 6], :5' TAA TCA AGC TTG ATT ACC CAC TGC ATT GTT CCT3'; EcoR I-R [SEQ ID NO. 7], :3' GGA ATT CCT GCA TTC TAG TTG TGG TTT GTC C 3'). PCR is performed to amplify the mTrkA-hFc gene. The amplified PCR product of the mTrkA-hFc gene and the pFLAG-CMV-1 vector (obtained from Sigma, St. Louis, Mo.) are ligated under the actions of restriction enzyme and ligase. Nucleotide sequence analysis is then performed to confirm the DNA sequence of the mTrkA-hFc/pFLAG-CMV-1 vector. The cDNA sequence of the ligand binding domain of the TrkA receptor from a mouse is appended to the Fc region of a human IgG via genetic engineering. The cytomegalovirus (CMV) promoter, which drives the expression of fusion protein in the whole body, is used as the promoter of the fusion gene (see FIG. 1A).

Figure 1B:
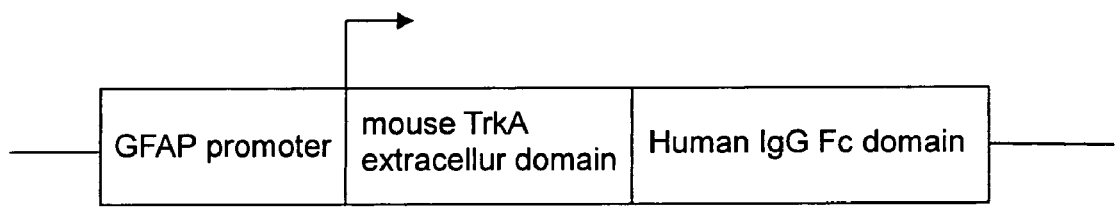
FIG. 1B is the gene map of the mTrkA transgenic vector with the GFAP promoter.

Using the mTrkA-hFc/pFLAG-CMV-1 vector as a template to design the PCR primer (SalI-upper [SEQ ID NO. 2]:

5' ACGCGTCGACACCATGTCTGCACTTCTGAT3';
Blp1-lower [SEQ ID NO. 9]: 5' GCTNAGCCAATGGT-
GATGGTGATGATG3'). PCR is performed to amplify the
mTrkA-hFc gene. The amplified PCR product of mTrkA-
hFc and the pGFA2-clac vector (glial fibrillary acidic pro-
tein, GFAP, and obtained from Dr. Michael Brenner, Uni-
versity of Alabama at Birmingham) are ligated under the
actions of restriction enzyme and ligase. Nucleotide
sequence analysis is then performed to confirm the DNA
sequence of the mTrkA-hFc/pGFA2-cLac vector. The cDNA
sequence of the ligand binding domain of the TrkA receptor
from a mouse is appended to the Fc region of a human IgG
via genetic engineering. The GFAP promoter, which directs
brain cell-specific expression (Segovia, 1998, "Differentia-
tion-dependent expression of transgenes in engineered astro-
cyte cell lines" Neurosci Lett 242:172-176; Shi, 2001,
"Brain-specific expression of an exogenous gene after i.v.
administration" PN 98(22):12754-127; Palu, 2001, "Gene
therapy of brain and endocrine tumors" Croat Med J. 42(4):
473-477; Morimoto, 2001, "Elevated blood pressure in
transgenic mice with brain-specific expression of human
angiotensinogen driven by the glial fibrillary acidic protein
promoter" Circ Res. 89:365-372; Zamorano, 2003, "Tran-
scriptionally mediated gene targeting of gas1 to glioma cells
elicits growth arrest and apoptosis" J Neurosci Res. 71:256-
263), in the pGFA2-cLac vector is used as the promoter of
the fusion gene to localize the expression of the fusion
protein in the brain area (in specific regions of the embryonic
central nerve system) (see FIG. 1B).

II. Production of TrkA-trap Transgenic Mouse:

Pronuclei microinjection is the method most extensively
used in the production of transgenic mice. Pronuclei micro-
injection involves injecting a small quantity of a transgenic
vector liner DNA segment into the pronucleus of a recently
fertilized embryo (the 3 kb DNA segment is isolated from
the mTrkA-hFc/pFLAG-CMV-1 vector using Xho I and Spe
I and the 6KB DNA segment is isolated from the mTrkA-
hFc/pGFA2-clac vector using Bgl I). The embryo is col-
lected from the oviduct of the donor mouse and is transferred
to a microinjection workstation. The embryo is stabilized
and fixed onto the end of a holding pipette, and DNA
solution is injected sequentially through the zona pellucida,
the oocyte membrane and the male pronuleus membrane
with adequate volume to see an obvious swelling of the
pronuleus. The injected embryos are then implanted into a
pseudopregnant recipient under a sterilized condition. The
transgenic efficiency is determined by performing a PCR
assay or a southern blot assay. A first-generation transgenic
animal that develops directly from a microinjected embryo
and carries the transgene is known as a founder animal. The
founder, with the transgene capable of functional expres-
sion, can breed for hemizygotes or a homozygotes.

III. Transgenic Mice Verification:

(1) Using PCR to Verify TrkA-trap Transgenic Mice

After extracting the chromosome DNAs from the tail
specimen of the transgenic mice, by using the DNAs as the
template, the polymerase chain reaction (PCR) is performed
with primers TrkA-Tg-for [SEQ ID NO. 10] (5' GGTG-
GAGCAGCATCATTGGTGCATC) and HFc-Tg-rev [SEQ
ID NO. 11] (5' CTCAGGGTCTTCGTGGCTCACGTC) for
30 cycles under 95° C. 30 seconds, 62° C. 30 seconds, and
72° C. 30 seconds, to amplify the transgene incorporated in
the chromosome. After the PCR reaction is completed, the
PCR products are analyzed by electrophoresis in 1.5%
agarose gel (110V, 20 minutes); the expected PCR product
of the transgene TrkA-hFc (TrkA-trap) is at a band of 400
base pairs.

Figure 2:
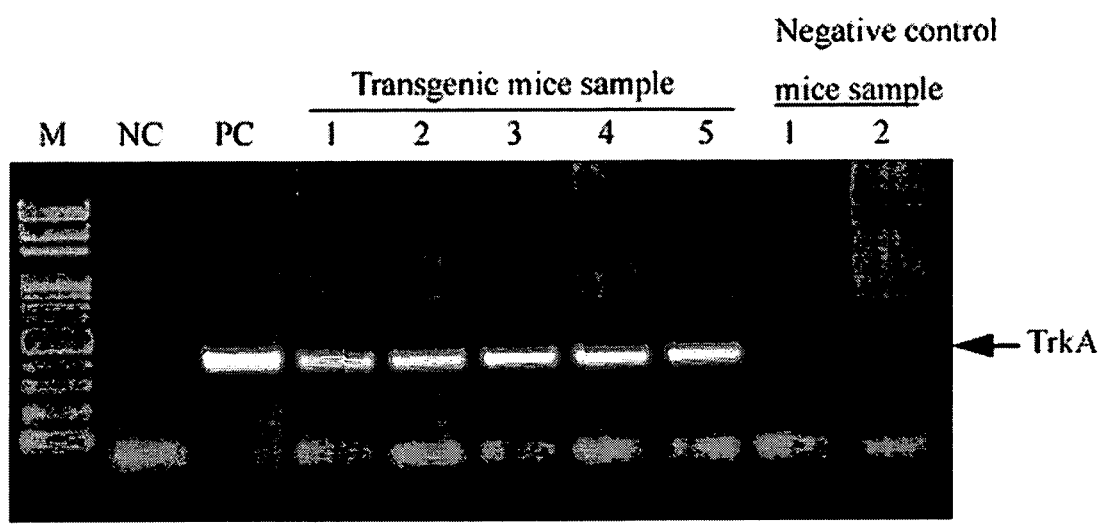
FIG. 2 shows the analysis results of the electrophoresis.

FIG. 2 shows the analysis results of the electrophoresis,
where M represents the DNA ladder marker, NC represents
the negative control by using water as the template, PC
represents the positive control by using the vector DNA as
the template, transgenic mice samples No. 1-5 are the PCR
products of chromosome DNA from different transgenic
mice and the negative control mice samples No. 1-2 are the
PCR products of chromosome DNA from non-transgenic
mice. The specimen DNAs containing the transgene TrkA-
HFc is evidenced by the presence of the PCR product of 400
base pairs, which verifies the transgenic mouse (mouse
having the transgene).

(2) Using Southern Blot Hybridization to Verify TrkA-trap
Transgenic Mice:

DIG DNA Labeling and Detection kit (Cat.No.1745832
purchased from Roche Inc.) is used to label Digoxigenin
(DIG) to TrkA-trap vector DNA, as the hybridization probe.
The PCR verified product(s) is run in 0.8% agarose gel
electrophoresis and then the DNAs on the agarose gel are
transferred (blotted) to the HyBond N+ blotting membrane
through the capillary action. The specific TrkA-trap DNA
probes (25 ng/ml) labeled with DIG are added to the
membrane for hybridization with the PCR product(s) from
the transgenic mice, under 42° C. for 16 hours. After
removing the solution containing the probes, the buffer No.
1 (2×SSC+0.1% SDS) is added and shaking in the room
temperature for 5 minutes, and then the buffer No. 2 (0.5×
SSC+0.1% SDS) is added and shaking under 42° C. for 30
minutes, in order to remove the probes in excess or the
non-specifically binding probes. Afterwards, the solution
containing the conjugate of anti-DIG-antibody was added to
the membrane and incubated in the room temperature for
one hour. As the incubation complete, the solution contain-
ing the antibody is removed and the washing buffer (0.1M
Maleic acid, 0.15M NaCl pH7.5 and 0.3% Tween 20) is
added to wash off the remained antibody. Then alkaline
phosphatase (anti-DIG-AP) is added and reacted with the
membrane in the room temperature for 60 minutes to detect
DIG on the membrane. Finally, the substrate that become
luminescent when catalyzed by alkaline phosphatase (CDP-
star chemiluminescent substrates®, purchased from Applied
Biosystems Inc.) is added and incubated, and the resultant
luminescence is exposed to the film, to identify the existence
of the transgene.

Figure 3:
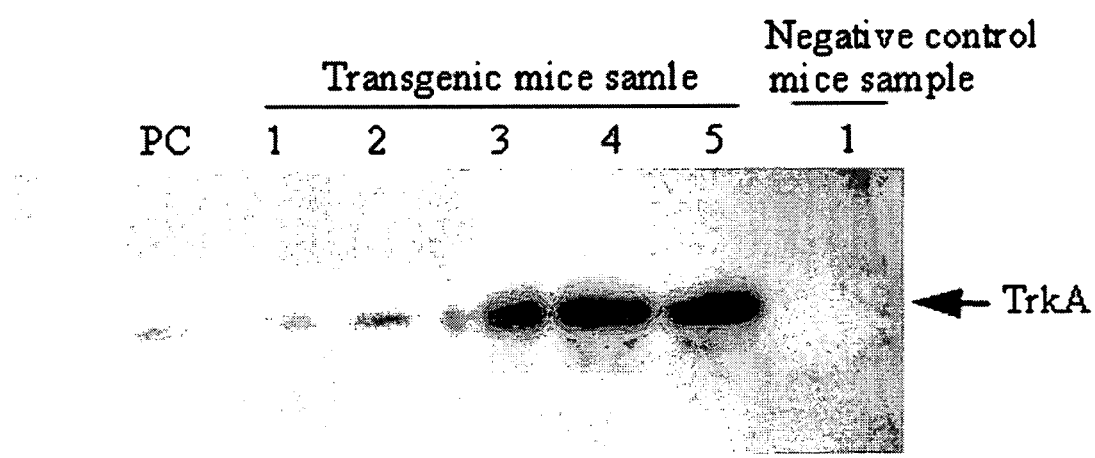
FIG. 3 shows the analysis results of the Southern blot hybridization.

FIG. 3 shows the results of Southern blot hybridization,
where PC represents the positive control of the PCR prod-
ucts by using the vector DNA as the template, transgenic
mice samples No. 1-5 are the PCR products of chromosome
DNA from different transgenic mice and the negative control
mice samples No. 1 is the PCR products of chromosome
DNA from the non-transgenic mouse. The PCR products of
DNAs containing the transgene TrkA-hFc can be hybridized
with the probes to generate luminescence signals, while no
signal is shown from the PCR products without the trans-
gene. Therefore, the transgenic mouse (mouse having the
transgene) can be verified.

(3) Using Western Blot Hybridization to Verify TrkA-trap
Transgenic Mice:

The brain tissue of the transgenic mice is frozen in liquid
nitrogen, grinded by the tissue grinder and homogenized in
the buffer solution, followed by centrifugation under 4° C. in
13000 rpm for 10 minutes; the precipitate is removed and the
supernatant is measured by BCA kit (from Pierce Biotechnology Inc.) so as to quantify the protein. After running 100 μg of the protein in SDS-polyacrylamide gel (SDS-PAGE) electrophoresis, the protein is blotted to the PVDF blotting membrane. As the blotting is complete, 5% skim milk is added for blocking, in the room temperature and shaking for an hour. Rabbit anti-Human IgG Fc antibody (2.4 μg/ml, purchased from Jackson ImmunResearch Laboratories Inc.) is added and incubated under 4° C. for 16 hours. As the incubation is complete, the solution containing the antibody is removed and the washing buffer (TBST) is added to the paper in the room temperature and shaking for several times to wash off the remained antibody. Afterwards, peroxidase-conjugated Goat anti-Rabbit IgG antibody (0.1 μg/ml, purchased from Jackson ImmunResearch Laboratories Inc.) is added to the paper in the room temperature and shaking for two hours for reaction, followed by removing the solution containing the antibody and adding the washing buffer (TBST) in the room temperature and shaking for several times to wash off the remained antibody. The blotting paper is incubated with enhanced chemiluminescence substrate (ECL from Pierce Biotechnology Inc.) for visualization. The ECL substrate is catalyzed by peroxidase to generate luminescence signals. The film is used to detect the luminescence signals to verify the expression of the transgenic protein in the brain tissue.

Figure 4:
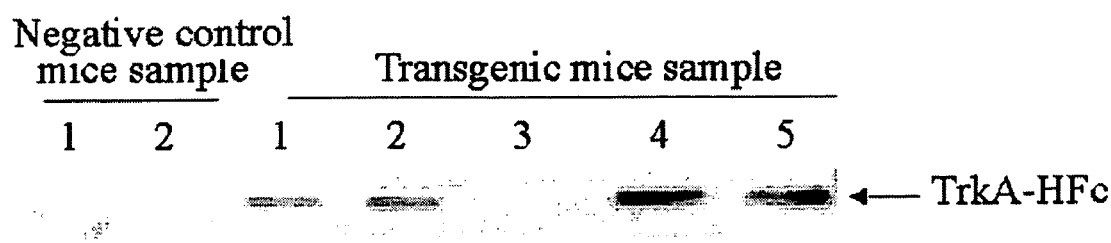
FIG. 4 shows the analysis results of the Western blot hybridization.

FIG. 4 shows the results of the Western blot hybridization, where the negative control mice samples No. 1-2 are brain tissue specimens of the non-transgenic mice, transgenic mice sample No. 1-5 are brain tissue specimens of different transgenic mice. For the transgenic mice sample No.1, 2, 4 and 5, the expression of the transgenic protein TrkA-hFc are found in the brain tissue specimens. On the other hand, no expression of the protein TrkA-hFc is found for non-transgenic mice under the same reaction conditions, considered as the negative control.

(4) Morris Water Maze:
(a) Water Maze

The water maze includes a stainless-steel round pool (in a diameter of 90 cm, a height of 30 cm and having a wall thickness of 15 mm) full of water and a platform beneath the water surface (platform with a diameter of 10 cm and a height of 22 cm, located 1 cm beneath the water surface), and the water temperature stays around 23±1° C. The pool is divided into four quadrants (I, II, III and IV) by the computer and divided into three concentric rings (A, B and C; from the center to the circumference). The recording system used for the tests includes VIDEOMEX-V video tracking, video camera and video monitor (from Columbus Instruments International Co.), using the software Water Maze Program (from Columbus Instruments International Co.).

(b) Learning Memory Test

In this invention, the well-known Morris water escape task is used to study learning in mice (using the Morris water maze). The procedure is as follows.

(i) Spatial performance: The pool is divided into four quadrants and the platform is located in the B section in the quadrant IV. The tested mice are respectively placed into the four quadrants in sequence following the order: I, II; III; IV; and trained each time for 60 seconds for consecutive four days. If the mouse finds the platform in 60 seconds, it is allowed to sit on the platform for 15 seconds and then removed from the maze for a break for 15 minutes. If the mouse can not find the platform in 60 seconds, it is placed on the platform to sit for 15 seconds and then removed from the maze for a break for 15 minutes. Record the amount of time the mouse spent on swimming in the pool. The above procedure is performed to test the spatial performance of the mice.

(ii) Reference memory: After the platform is removed, the tested mouse is placed in the quadrant I, and consecutively recording for 60 seconds to record the swimming path of the mouse and the amount of time spent on the original platform. The above procedure is performed to test the reference memory of the mice.

Figure 5:
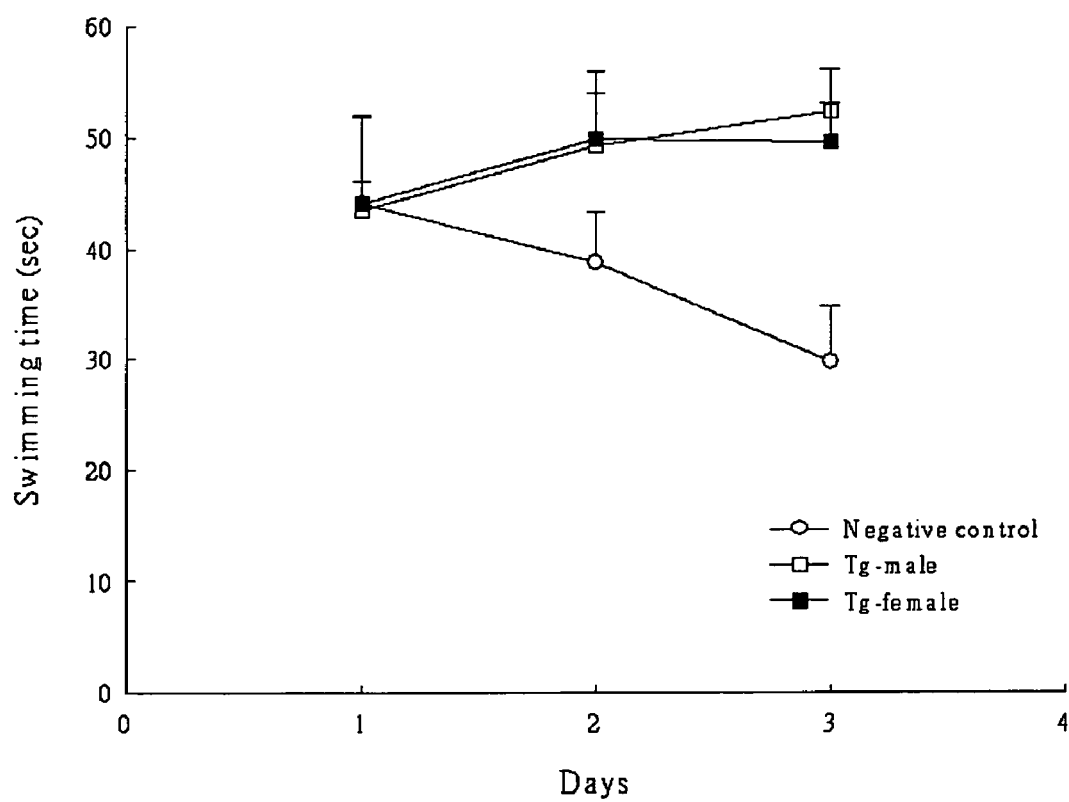
FIG. 5 shows the results of the Morris water maze.

FIG. 5 shows the results of the Morris water maze. The 7 month old mice are placed in Morris water maze to analyze their learning memory abilities. In the graphic diagram of FIG. 5, the vertical axis represents the swimming time of the mice to reach the platform, while the longitudinal axis represents the training period (in days). For a normal mouse with acceptable learning memory ability, the swimming time required to arrive at the platform keeps decreasing as the training days increase. However, the same pattern can not be observed for the transgenic mice, which indicates deficiency in the learning and memory ability and failure in leanings for the transgenic mice. Herein, the negative controls are non-transgenic normal mice, "Tg-male" represents male transgenic mice and "Tg-female" represents female transgenic mice.

(5) Brain Pathological Sections:
(a) Scarified Animals

The mice are sacrificed under anesthetization and fixed through cardiovascular perfusion with 4% paraformaldehyde, and their brain tissues are removed and immersed in 30% sucrose solution for dehydration. Once the brain sinks, the brain tissue is cut into 25 μm sections in a cryostat and preserved in the cryoprotectant at −20° C. for later staining.

(b) Bielschowsky Silver Stain

Bielschowsky's silver staining can be used for staining nerve fibers, axons, neurofibrillary tangles and senile plaques on sections.

The sections are placed on the slides and immersed in 4% silver nitrate solution in the dark for 4 hours. Afterwards, the slides are washed and treated with ammoniacal silver for 1 minute, followed by fixation with 10% formalin for 10 minutes. After treated with gold chloride for color enhancing, the slides are dipped in 5% sodium thiosulfate solution for 2 minutes. The sections are then washed, dehydrated, cleared and mounted with resinous medium. The sections are microscopically examined.

Figure 6:
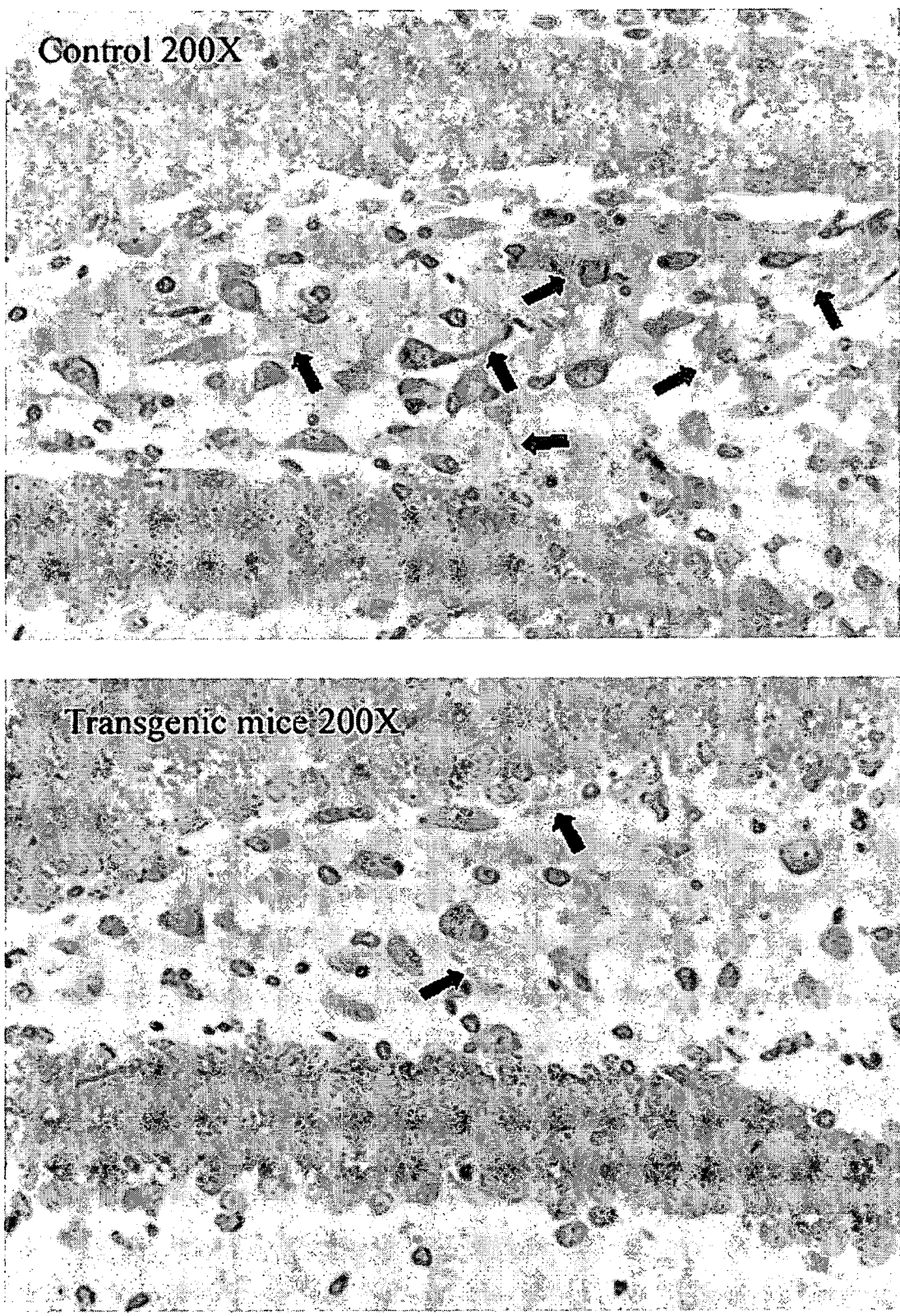
FIG. 6 shows the observed results of the stained sections under the microscope (200×).

FIG. 6 shows the observed results of the stained sections under the microscope (Labphoto-2, Nikon, 200×). After the staining, the color black is observed for the nerve fibers, axons, neurofibrillary tangles and senile plaques, while the background color is yellow to brown. When comparing the sections of the control mice and the transgenic mice, the hippocampus of the transgenic mice has less neurons and shorter nerve fibers (neurons and nerve fibers are marked by arrows), which indicates that the brain of the transgenic mice has neurodegeneration.

IV. Drug efficiency analysis:

The commonly prescribed drug donepezil (brand name: Aricept) for the Alzheimer's disease (AD) is used to evaluate the drug efficiency. Donepezil inhibits acetylcholinesterase, an enzyme responsible for the destruction of one neurotransmitter, acetylcholine.

Seven month old normal mice and seven month old transgenic mice are tested by orally feeding the drug (0.75 mg/kg) for three days. The behaviors of the tested mice are analyzed by pacing the mice in the Morris water maze to evaluate their learning memory abilities.

Figure 7:
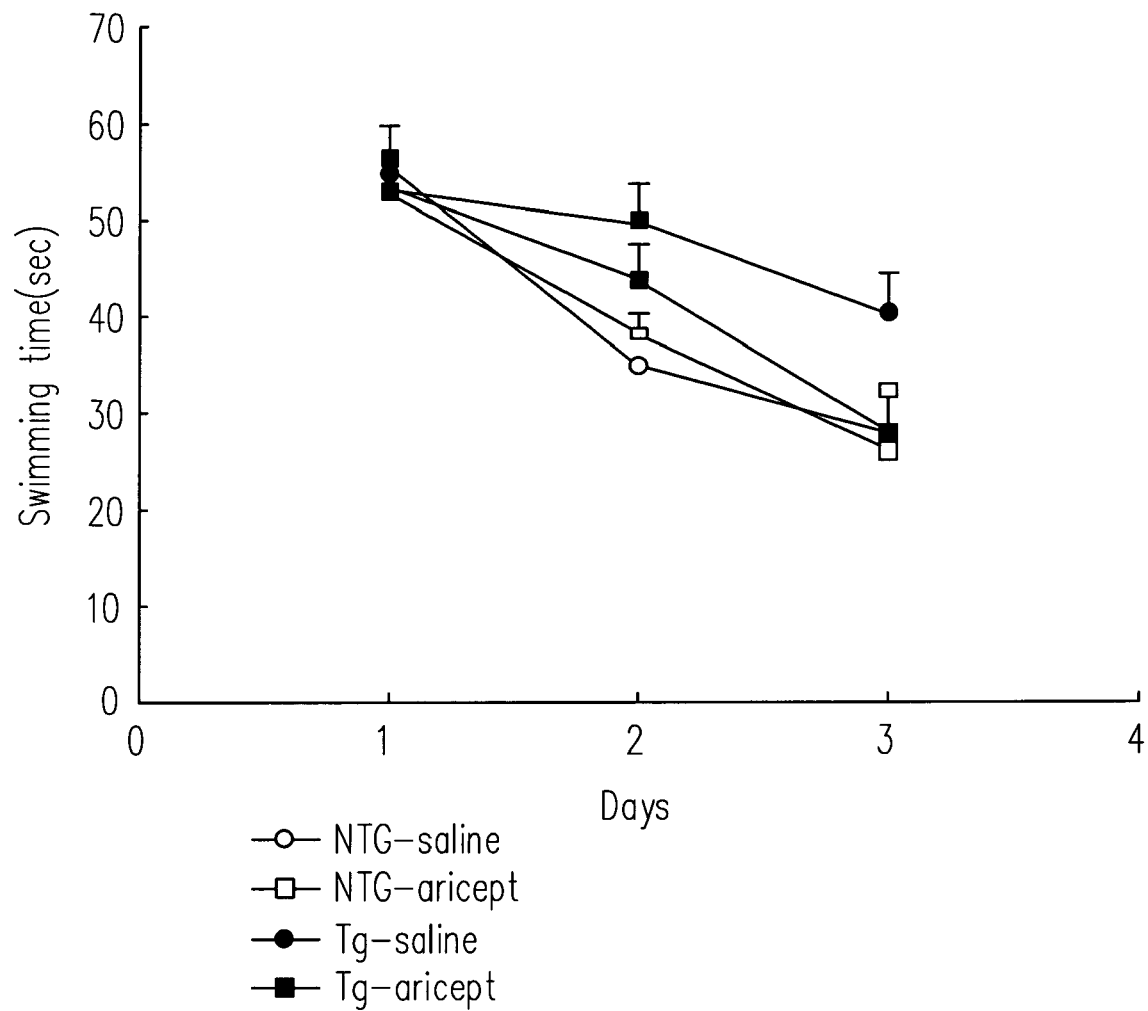
FIG. 7 shows the results of the Morris water maze for drug efficiency analysis.

FIG. 7 shows the results of the Morris water maze for drug efficiency analysis. In the graphic diagram of FIG. 7, the vertical axis represents the swimming time of the mice to reach the platform, while the longitudinal axis represents the training period (in days), where NTG-saline represents normal mice feeding with saline, NTG-aricept represents normal mice feeding with the drug donepezil, Tg-saline represents transgenic mice feeding with saline, and Tg-aricept represents normal mice feeding with the drug donepezil. It clearly shows that transgenic mice taking the drug donepezil have better learning memory abilities than the transgenic mice feeding with saline. For the normal mice, the mice behave similarly no matter either using the drug or saline. This indicates that the drug donepezil can improve the learning memory ability for the transgenic mice with the transgene TrkA-trap. Therefore, the transgenic mouse provided in the present invention has the potentials as the animal model for screening the drug candidates for treating neurodegenerative diseases, such as the Alzheimer's disease.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A transgenic mouse whose genome comprises a recombinant DNA sequence comprising:

a cytomegalovirus (CMV) promoter; and a transgene comprising a DNA sequence of a ligand binding domain of a TrkA receptor from a donor non-human mammal and a constant region (Fc region) of a human immunoglobin G (IgG), wherein the promoter and the transgene are operatively linked to each other in the transgenic mouse, wherein the transgenic mouse exhibits neuronal loss and shorter nerve fibers in the hippocampus and learning memory loss.

2. The transgenic mouse of claim 1, wherein said mouse is fertile and transmits the transgene to its offspring.

3. A cell isolated or derived from the transgenic mouse of claim 1.

4. A method of evaluating potential therapeutic effects of a compound in a transgenic mouse, for treating a hippocampal lesion in a mammal, comprising:

administrating the compound to the transgenic mouse whose genome comprises a cytomegalovirus (CMV) promoter and a recombinant DNA sequence comprising a DNA sequence of a ligand binding domain of a TrkA receptor from a donor non-human mammal and a constant region (Fc region) of a human immunoglobin G (IgG), wherein the promoter and the transgene are operatively linked to each other in the transgenic mouse; and determining the potential therapeutic effects of the compound on the transgenic mouse by identifying improvement in learning and memory behavior of the transgenic mouse.

* * * * *